(12) United States Patent
Bronkhorst et al.

(10) Patent No.: US 9,895,498 B2
(45) Date of Patent: Feb. 20, 2018

(54) FLUID WARMING SYSTEM

(71) Applicant: THE SURGICAL COMPANY INTERNATIONAL B.V., Amersfoort (NL)

(72) Inventors: Joris Bronkhorst, Enschede (NL); Jeroen Hermanus Johannes Wijlens, Haaksbergen (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 38 days.

(21) Appl. No.: 15/070,144

(22) Filed: Mar. 15, 2016

(65) Prior Publication Data
US 2016/0271342 A1    Sep. 22, 2016

(30) Foreign Application Priority Data
Mar. 16, 2015    (EP) .................................... 15159290

(51) Int. Cl.
*F28F 7/00* (2006.01)
*A61M 5/44* (2006.01)
(Continued)

(52) U.S. Cl.
CPC .............. *A61M 5/44* (2013.01); *A61F 7/00* (2013.01); *F24H 1/142* (2013.01); *F24H 9/02* (2013.01);
(Continued)

(58) Field of Classification Search
CPC .............. A61M 5/44; A61M 2205/121; A61M 2205/127; A61M 2205/3368;
(Continued)

(56) References Cited

U.S. PATENT DOCUMENTS 5,195,976 A * 3/1993 Swenson .......... A61M 5/16886
604/113
5,381,510 A    1/1995 Ford et al.
(Continued)

FOREIGN PATENT DOCUMENTS

EP    0 488 769    6/1992
WO    WO 2011/015912    2/2011

OTHER PUBLICATIONS

Search Report for EP 15159290.4, dated Jul. 17, 2015, 10 pages.

*Primary Examiner* — Davis Hwu
(74) *Attorney, Agent, or Firm* — Nixon & Vanderhye P.C.

(57) ABSTRACT

There is disclosed a heater unit (1600) for conductively heating a removable heat exchanger unit (1602) via a heat transfer surface of the heat exchanger unit, the heater unit comprising: a body portion (1610) for receiving the heat exchanger unit (1602); a flexible heating element (1604) which, in use, makes thermal contact with the heat transfer surface of the heat exchanger unit; a compressible portion (1606) disposed on the distal side of the flexible heating element (1604) relative to the heat exchanger unit (1602) when received; and a biasing arrangement (1608) operable, in use, to distribute a transverse compression force across the arrangement formed from the compressible portion (1606), the heating element (1604) and the heat exchanger unit (1602), whereby the compression force causes the heating element (1604) to be urged towards the heat transfer surface of the heat exchanger unit (1602) and the compressible portion, in conjunction with the compression force, causes the heating element (1604) to conform more closely to the shape of the heat transfer surface.

19 Claims, 16 Drawing Sheets

(51) Int. Cl.
  *F24H 1/14* (2006.01)
  *F24H 9/02* (2006.01)
  *F28F 13/00* (2006.01)
  *A61F 7/00* (2006.01)
  *H05B 3/58* (2006.01)
  *F24H 9/20* (2006.01)
  *H05B 3/20* (2006.01)

(52) U.S. Cl.
  CPC ............... *F28F 13/00* (2013.01); *H05B 3/58* (2013.01); *A61M 2205/121* (2013.01); *A61M 2205/127* (2013.01); *A61M 2205/3368* (2013.01); *A61M 2205/3653* (2013.01); *F24H 9/2028* (2013.01); *F28F 2013/008* (2013.01); *H05B 3/20* (2013.01); *H05B 2203/021* (2013.01)

(58) Field of Classification Search
  CPC .. A61M 2205/3653; A61F 7/00; F24H 1/142; F24H 9/02; F24H 9/2028; F28F 13/00; F28F 2013/008
  USPC .......................................................... 165/46
  See application file for complete search history.

(56) References Cited

U.S. PATENT DOCUMENTS

| | | | |
|---|---|---|---|
| 6,254,624 B1* | 7/2001 | Oddsen | .................. A61B 17/08 606/150 |
| 2004/0072334 A1 | 4/2004 | Benett et al. | |
| 2005/0008354 A1 | 1/2005 | Cassidy | |
| 2011/0098642 A1 | 4/2011 | Cassidy | |
| 2014/0207063 A1 | 7/2014 | Hyun et al. | |
| 2014/0221960 A1* | 8/2014 | Stihler | ................. H05B 1/0244 604/500 |

\* cited by examiner

TOP VIEW

CROSS SECTION AT X-X'

BOTTOM VIEW

TOP VIEW

SIDE VIEW

END VIEW

TOP VIEW

BOTTOM VIEW

FLUID WARMING SYSTEM

This application claims priority to EP Patent Application No. 15159290.4 filed 16 Mar. 2015, the entire contents of which is hereby incorporated by reference.

FIELD OF THE INVENTION

The present invention relates to heater unit for conductively heating a removable heat exchanger unit, and a fluid warming system including such a heater unit and at least one heat exchanger unit. The invention is particularly applicable to, though not limited to, the warming of intravenous (IV) fluids for delivery to a patient.

BACKGROUND TO THE INVENTION

In some cases it is convenient or necessary to use a fluid warmer to heat a continuously-flowing fluid to a target temperature or range of temperatures, for example to warm intravenous (IV) fluids to body temperature before delivery to a patient.

In a conventional device the fluid flows through an appropriate conduit, and a conductive heater element transfers heat to the fluid through intervening layers such as the conduit walls. In some cases, such as in the IV fluid warmer mentioned above, the conduit is releasably attachable, and may for example be a disposable cassette which is inserted into the fluid warmer unit prior to use.

US 2011/0098642, the contents of which are hereby incorporated by reference, concerns one such fluid warmer. In this device, the IV fluid passes through a disposable 'set' which is held in place by slideable covers. When the covers are closed, they apply pressure to the set to compress it towards a heater assembly, creating better thermal contact between the assembly and the set. The size and unevenness of the applied pressure can cause relatively high stresses and deformation of the heater assembly and other elements of the fluid warmer device, reducing efficiency and the lifetime of the device.

The present invention seeks to address these and other problems in the prior art.

SUMMARY OF THE INVENTION

In a first aspect of the invention, there is provided a heater unit for conductively heating a removable heat exchanger unit via a heat transfer surface of the heat exchanger unit, the heater unit comprising: a body portion for receiving the heat exchanger unit; a (typically planar) flexible heating element which, in use, makes thermal contact with the heat transfer surface of the heat exchanger unit; a compressible portion disposed on the distal side of the flexible heating element relative to the heat exchanger unit when received; and a biasing arrangement operable, in use, to distribute a transverse compression force across the arrangement formed from the compressible portion, the heating element and the heat exchanger unit, whereby the compression force causes the heating element to be urged towards the heat transfer surface of the heat exchanger unit and the compressible portion, in conjunction with the compression force, causes the heating element to conform more closely to the shape of the heat transfer surface.

In this arrangement, potential deformation and consequent degradation of the heating element and heat exchanger unit can be reduced by virtue of a more even distribution of forces through the compressible portion.

Preferably the biasing arrangement is operable to improve the physical and/or thermal contact between the heating element and heat exchanger unit. The improvement may be, for example, in terms of increased surface contact or uniformity, and/or to correct for surface abnormalities in the heat exchanger unit or heating element, or any material or layer inbetween. The term 'receiving' as used above preferably connotes merely being operable to cooperate physically with, so as to ensure the physical contact between the membrane and heat exchanger unit. The term may for example cover embodiments including the permanent attachment of a fluid conduit or other transport unit to the body portion.

The compressible portion is preferably formed from an elastic material, such as silicon foam. Preferably the compression force is a substantially uniform force and is distributed substantially uniformly across the heater contact area (that is to say, may differ by less than 20, 10, 5, 2, 1 or 0.5% across the contact area). Preferably the compressible portion distributes as well as transmits the compression force, creating a more uniform force, and may as noted conform to an appropriate degree (depending on the thickness, compressibility and other material and physical properties of the compressible portion, and so on) to the surface of the heat exchanger unit and/or heating element to correct for irregularities in the surface or physical contact. The physical and/or material properties of the compressible portion may be variable as necessary to adapt to different types or manufacturing tolerances in relation to the heat exchanger unit and so on.

The biasing arrangement and/or compressible portion is typically distributed across substantially the entire area of the heating element, but need not be. Either may for example extend beyond the heating element by more than 1, 2, 5, 10, 20, 50 or 100%, for example (at least in part), or the heating element may instead extend by a similar amount, and so on.

Preferably, in use, the biasing arrangement has an effective first modulus of elasticity, and the compressible portion has an effective second modulus of elasticity, where the second modulus is preferably smaller than the first. A similar comparison can be made for spring constants and the like. The moduli/spring constants may be variable in use or under different conditions, for example due to non-linear material responses of the relevant components to applied compression forces, temperatures, and so on. Preferably the body portion is rigid, at least relative to the compressible portion and/or biasing arrangement, and preferably has a larger effective modulus of elasticity than either (and preferably at least 10, 50, 100, 500 or 1000 times greater).

The heat exchanger unit could, for example, be a fluid transport device such as a pipe or other fluid conduit, but is preferably a specialised heat transfer device with a relatively large surface area per volume of conduit exposed to the membrane, for example having a wide, narrow planar flow, or incorporating a serpentine path, and may either enclose or be interposed within a fluid transmission line. The heater unit may include a thermally-conductive phase change or other (for example liquid) layer between the membrane and the heating element, which can further improve the thermal conductivity between the heating element and (ultimately) the fluid to be warmed. Preferably the membrane contacts a heat-transfer surface and/or a substantial portion of the exposed surface area of the heat exchanger unit, for example contacting at least 50, 60, 70, 80, 90 or 95% of the surface of the heat exchanger unit that is exposed to the heater unit.

The heater unit preferably further comprises a thermally-conductive membrane which, in use, physically contacts the heat exchanger unit and separates the heat exchanger unit from the heating element. The membrane is preferably attached to the body portion. The thermally-conductive membrane is preferably an electrical insulator, and preferably both or either of the membrane and heating element are flexible. Preferably the membrane (and more preferably also the heating element layer) is attached to the body portion. It may be partially or fully attached at the periphery, for example around the circumference of the membrane by any appropriate attachment. The membrane is preferably compressed against at least one seal incorporated in the body portion, for example by screws, rivets or other fixing means, which may join the body portion to another portion of the heater unit pressing on the membrane. The membrane may instead or additionally be glued or otherwise attached physically to the body portion. In an alternative embodiment, the membrane may instead 'float' or otherwise move independently relative to the body portion, with appropriate means to ensure an adequate seal between the membrane and body portion.

Because of the above-mentioned constraints on the membrane, the principal movement within the heater unit is of the compressible components (in particular the compressible portion) towards the flexible heater and heat exchanger unit. Thus less deformation is in general required of the heater, which can thus enjoy a longer lifetime, and there is less risk of air inclusions between the membrane and the heat exchanger unit. By fixing the membrane to the body portion, there is accordingly also a simplification of the seals between the membrane and the body portion, where present and necessary.

The heater unit preferably further comprises a retaining arrangement for releasably retaining the heat exchanger unit. The heat exchanger unit may in this case, for example, be a disposable or reusable cassette or other appropriate system, for example within a medical context, where fluid-contacting surfaces are frequently required to be disposed of or removed for sterilization. The present invention can be suited to these sorts of applications due to minor misalignments which may be expected in the course of insertion and/or replacement of the heat exchanger unit, and minor variations in the shape of different heat exchanger units due to manufacturing tolerances and the like.

Preferably the biasing arrangement is operable to increase the compression force when the heat exchanger unit is retained by the retaining arrangement. In this case, when the heat exchanger unit is removed, conversely, the compression force will be reduced (for example to less than 75, 50, 40, 30, 20, 15, 10, 5, 2, 1 or 0.5% of its maximum value). The compression force may be increased at the same moment that the unit is retained, during only part of the retaining operation, or otherwise in general prior to use of the heater unit after it is retained. This can reduce the wear on the compression portion and the heating element.

The retaining arrangement preferably includes a moveable arrangement, typically including at least one of a sliding portion, lever, and rack and pinion arrangement. Preferably one sliding portion is provided, allowing one end of the heater unit to be clamped or hand-held in place, allowing greater control of the slider and improved ergonomic handling.

The moveable arrangement is preferably operable to transmit a force to the biasing arrangement by means of a wedge, preferably attached to a sliding portion as above-mentioned, and a plunger, which is preferably arranged to cooperate with the wedge and be compressed when the sliding portion is closed so as to retain the heat exchanger unit. The plunger preferably includes a rotating member (such as a wheel) which, in use, is in contact with the wedge, whereby contact friction between the plunger and the wedge can be mitigated. Alternatively, the plunger may simply slide over the wedge, with an appropriately low friction surface being provided on the latter, which can make the assembly easier to clean and/or maintain.

Preferably the biasing arrangement is operable to maintain a minimum compression force when the heat exchanger unit is not retained by the retaining arrangement (nor any other, such as when the heat exchanger unit is removed, for example by opening a sliding portion as aforementioned. The compression force may for example be maintained at a minimum of between 1 and 20 Newtons, or more preferably between 2 and 15 N, 3 and 10 N, 4 and 6 N or substantially at 5 N, compared to a maximum compression force (when the heat exchanger unit is retained) of between approximately 20 and 200 N, more preferably between 40 N and 150 N, 60 N and 120 N, 80 and 110 N or substantially 100 N. Preferably an appropriate minimum compression force is selected so as to maintain tension in the membrane surface when the heat exchanger unit is absent or otherwise under substantially all conditions.

Preferably the biasing arrangement comprises a (first) spring, which is preferably pre-tensioned, for example with retaining fingers maintaining a minimum compression length of the spring. The use of a spring or other substantially elastically compressible member can reduce the amount of compression required in the compressible portion, which can help to avoid compression set and similar problems in the compressible material.

The biasing arrangement may further comprises a second spring which provides a smaller compression force than the first spring (1004) across a wider range of operating conditions (which operating conditions may for example encompass the retained and not retained states of the retaining arrangement as aforesaid, or any further states inbetween such as partially engaged, and so on). In other words, the second spring may apply a smaller but more continuously applied compression force than the first spring. This can help to provide the aforementioned feature whereby the biasing arrangement is operable to maintain the compression force when a heat exchanger unit is not retained by the retaining arrangement. The term 'more continuously applied' preferably connotes that the minimum and maximum forces applied by the second spring in use vary less as a percentage of the maximum force than for the first spring. For example, the first spring may apply a force between 0 and 100% of its maximum value (which may be considerable, such as 100 N), and the second spring may vary between only, say, 80 and 100% of its maximum value (which may be relatively small, such as 5 N). Either or both of the first and second spring may be replaced by a respective plurality of springs, which can improve the evenness of the distribution of forces across the compressible portion and beyond. In an alternative embodiment, the biasing arrangement comprises an inflatable member, for example, which can be inflated as appropriate to provide the necessary characteristics as aforementioned.

Preferably the biasing arrangement reacts against the body portion. The term 'reacting against' preferably connotes applying an equal and opposite reactive force equivalent to the compression force against the body. Preferably there is direct contact between the biasing arrangement and the body portion, which may be true of the aforesaid specific examples of biasing arrangements, but preferably the biasing arrangement and the body portion are separate and/or separable entities (for example the biaising arrangement is held within the body portion but not fixed to it, so it can be removed or replaced when the body portion is disassembled). Preferably the biasing arrangement is moveable independently of the body portion, which may include a base portion and a cover portion moveable relative to the base portion.

The compressible portion preferably includes at least one of a flexible foam, a plurality of springs, flexible rubber and flexible plastic. The compressible portion preferably exhibits low compression set and has relatively high heat resistance. The compression portion is preferably an elastomer, though it need not exhibit a linear elastic response or perfect memory. The compressible portion may in particular comprise silicon foam.

The heater unit preferably further comprises a rigid support layer, interposed between the biasing arrangement and the compressible portion, for distributing the compression force (at least more evenly) across the compressible portion. The compression frame may for example be a metal frame or other rigid material and/or structure, for example formed from aluminium for high strength and low weight.

The heater unit may in particular be used for warming intravenous fluids, and therefore will be useable with an appropriate range of flow rate, and will comprise sufficient temperature sensors, control systems and heater power to achieve the necessary range and control of temperature outputs.

In a further aspect of the invention there is provided a fluid warming system comprising a heater unit as aforementioned, and at least one heat exchanger unit configured for use with said heater unit.

Although various aspects and embodiments of the present invention have been described separately above, any of the aspects and features of the present invention can be used in conjunction with any other aspect, embodiment or feature where appropriate. For example apparatus features may where appropriate be interchanged with method features. References to single entities should, where appropriate, be considered generally applicable to multiple entities and vice versa. Unless otherwise stated herein, no feature described herein should be considered to be incompatible with any other, unless such a combination is clearly and inherently incompatible. Accordingly, it should generally be envisaged that each and every separate feature disclosed in the introduction, description and drawings is combinable in any appropriate way with any other unless as noted above) explicitly or clearly incompatible.

DESCRIPTION OF THE DRAWINGS

An example embodiment of the present invention will now be illustrated with reference to the following figures in which.

DETAILED DESCRIPTION OF AN EXAMPLE EMBODIMENT

Figure 1:
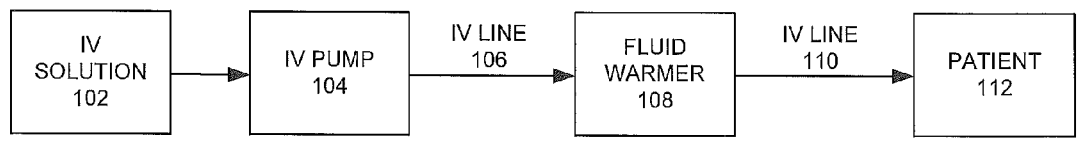
FIG. 1 is an overview of a typical application of a fluid warming system.

FIG. 1 is an overview of a typical application of a fluid warming system, in which an intravenous (IV) solution 102, which may for example be an aqueous solution of one or more medicines, is pumped by an optional IV pump 104 along an IV line 106 through a fluid warmer 108 and then along a further IV line 110 for intravenous insertion into the bloodstream of a patient 112. In the case of IV fluids, an outlet temperature typically in the region of 37-41° C. is desired. The IV solution may typically be presented at room temperature at around 20° C., but this temperature may vary. The flow rate of the IV fluid is typically controlled depending on the particular medicine or other fluid to be dispensed, and in dependence on properties of a patient or other end use of the fluid.

A gravity feed can be used instead of (or in addition to) the IV pump 104. In the absence of the IV pump 104 (or otherwise) the flow rate can be increased by pressurizing a bag or other receptacle containing the IV solution, or by any other appropriate means.

Figure 2:
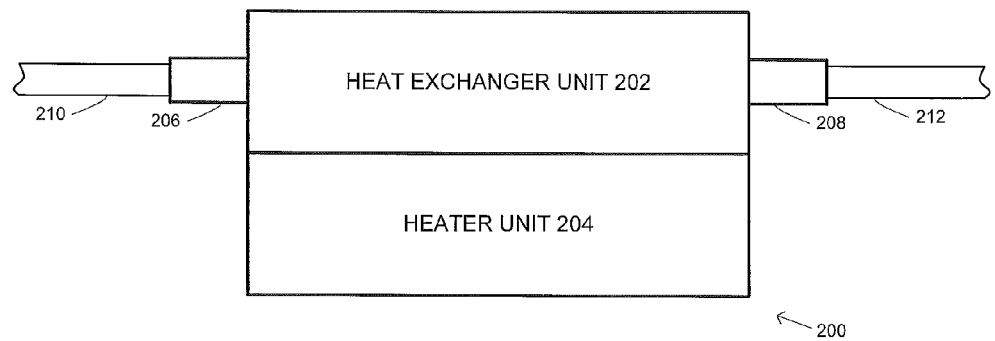
FIG. 2 schematic of the fluid warming system as used in FIG. 1.

FIG. 2 is a schematic of the fluid warming system as used in FIG. 1. The fluid warming system 200 of the present embodiment includes a heat exchanger unit 202 and a heater unit 204. The heat exchanger unit 202 includes an inlet 206 and an outlet 208 for attachment to a first IV line 210 and second IV line 212 respectively. An appropriate valve or seal (not shown) is provided on the inlet 206 and outlet 208. In use, the heat exchanger unit 202 is attached to the heater unit 204 to permit heat transfer between the two. The provision of a separate heat exchanger unit, typically in the form of a disposable cassette (see below), can improve the hygiene of the system and can reduce costs by allowing the most expensive part of the warming system to be (re)used indefinitely. In other fluid warming systems, the heat exchanger unit 202 may, for example, be integral to the heater unit 204, and other variations are of course possible.

Figure 3:
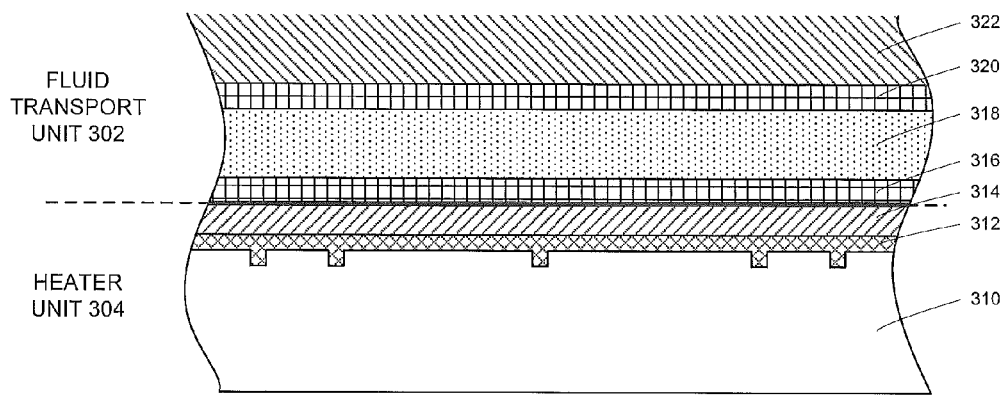
FIG. 3 is a schematic showing different layers of material forming part of the fluid warming system of FIG. 2.

FIG. 3 is a schematic showing different layers of material in one embodiment of the fluid warming system of FIG. 2. The figure is not to scale and is at least partially exaggerated on the vertical axis. In the figure the heat exchanger unit 202 and heater unit 304 are shown in the engaged configuration (as in use). In the heater unit 304, a foam layer 310 underlies a flex heater 312 which is mounted on a circuit board (not shown). A layer 314 of a thermally conductive but electrically insulating membrane covers the heater 312 to provide protection from environmental damage and electrical short circuit and the like. The heat exchanger unit 302 is coupled to the membrane layer 314 of the heater unit 304 by a parylene coating 316 (or suitable alternative) which covers a relatively thick layer 318 (for structural stiffness) of aluminium, which is separated from the fluid 322 in the fluid channel by another parylene coating 320. Any of the materials mentioned above may of course be replaced by any suitable alternative having appropriate thermal or electrical conductivity, structural stiffness and/or suitability for use in a medical or other setting.

In more detail, in the present embodiment, the membrane layer 314 is formed from a Kapton® (polyimide) sheet, and the heater layer 312 is formed from another Kapton® (polyimide) sheet with copper tracks laid thereon. A conductive paste/coating is provided between the two Kapton® layers 312, 314 but in variants of the present embodiment a thermally conductive phase change material may be provided, or both layers 312, 314 may be replaced by a single thin foil heater with an electrically insulative layer overlaid thereon. Other variants may of course be possible providing they satisfy the requirements of high thermal conductivity, heat resistance and electrical insulation between the heater element and the exposed heating surface of the heater unit. A silicon foam is used for the foam layer 310, but other materials may be provided which have low compression set and high heat resistance properties. Another variant using springs is described later.

Figure 4A:
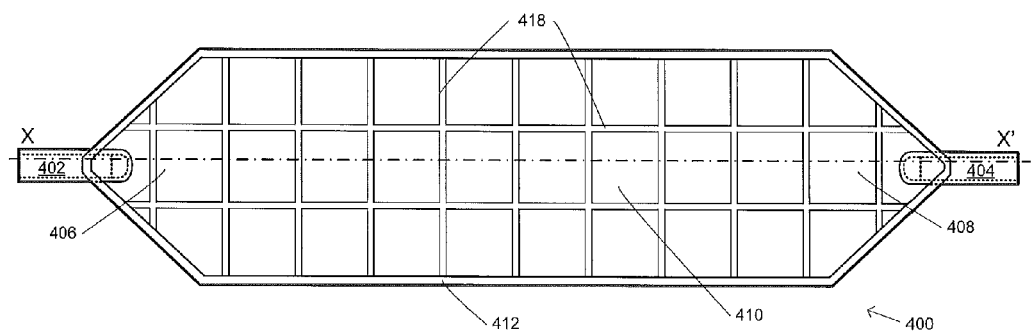
FIGS. 4A, 4B and 4C are illustrations of the heat exchanger unit of a specific embodiment of the fluid warming system of FIG. 2.
Figure 4B:
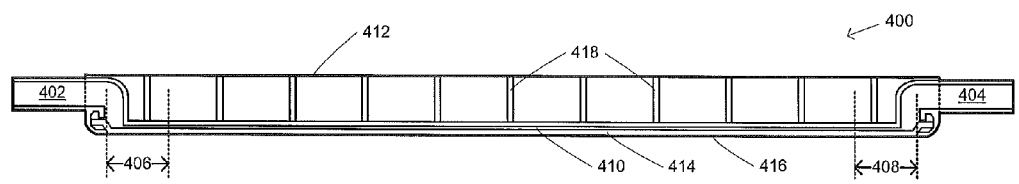
Figure 4C:
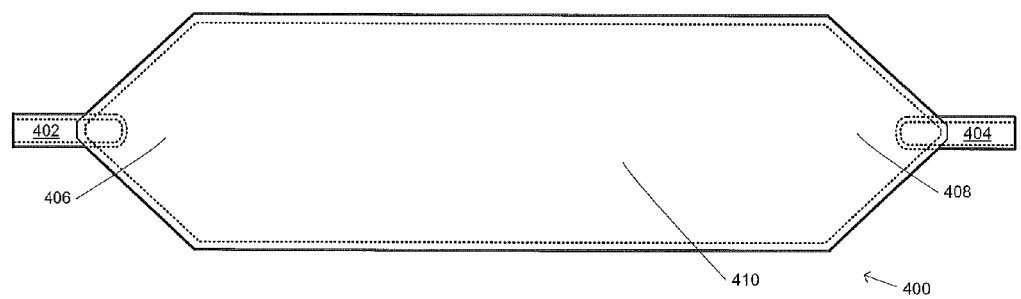

FIGS. 4A, 4B and 4C are illustrations (not to scale or necessarily complete or accurate in every detail) of the heat exchanger unit of a specific embodiment of the fluid warming system of FIG. 2. The heat exchanger unit 400 is provided in the form of a disposable cassette of mostly plastic construction (for sufficient rigidity at relatively low cost and little weight) with the bottom portion having a construction essentially as described above in relation to FIG. 3.

An inlet 402 and outlet 404 connector are shown, having a corresponding inlet portion 406 and outlet portion 408 of the fluid channel where it first makes relatively good thermal contact with the heater element. Sealing elements are provided, cooperating also with a plastic support structure 412, to ensure that the fluid channel 410 and the above-described layers 414 of parylene and aluminium remain well-bonded and in good thermal contact. At the base of the heat exchanger unit 400 there is provided a uniform flat surface 416 for making a good thermal contact with the heater unit. Interlocking vertical plastic webs 418 provide additional rigidity and strength.

FIGS. 5A, 5B and 5C are illustrations (not to scale or necessarily complete or accurate in every detail) of the heater unit of a specific embodiment of the fluid warming system of FIG. 2, suitable for use with the heat exchanger unit described above in relation to FIGS. 5A, 5B and 5C. The heater unit 500 of this embodiment includes a fixed first part 502 for receiving a heat exchanger unit (disposable cassette) as aforementioned and a slideably extendible second part 504 which surrounds most of the length of the first part 502 and locks the cassette in place when in use, as will be described in more detail below. A set of internally-disposed ribs (not shown) perform the function of guiding the slider and locking it into the fully open position. A heater element and control electronics (not shown) form part of the first, fixed part 502. The warmer may be battery-powered (not shown) or function using external power (for example from mains power with appropriate adaptor, not shown, or any appropriate AC or DC source), or both. Battery-powered versions may be particularly suitable for emergency or on-site use, for example, and mains-powered versions may be more suitable for general hospital use and the like.

A hand-grip 506 is provided at the fixed end in the form of a partial indentation in the body of the heater unit. This allows the heater unit 500 to be firmly grasped or clamped at the end of the fixed portion 502 while the sliding portion 504 is moved. The top 508 of the sliding portion is flush with the top of the heat exchanger unit/cassette 550 (shown in outline only in FIGS. 5A-5C), when it is present, and prevents the cassette 550 moving out of alignment when the wedge and plunger system (not shown) is activated. The fixed portion 502 of the heater unit 500 includes a recess 510 for receiving the disposable cassette 550 for ease of insertion and retention. At the bottom of the heater unit 500, the lower surface tapers up to a raised surface 512. The purpose of the taper will be explained below in relation to the wedge and plunger (not shown).

In a variant of the present embodiment, ribs (not shown) may be provided on the sliding portion 504 for ergonomic reasons and to provide extra structural strength and resistance to bending moments. Metal reinforcement bars may be provided in addition to or as an alternative to the ribs.

In alternative embodiments a rack and pinion system or a lever mechanism replace the sliding mechanism. Other variants are of course possible.

Figure 5A:
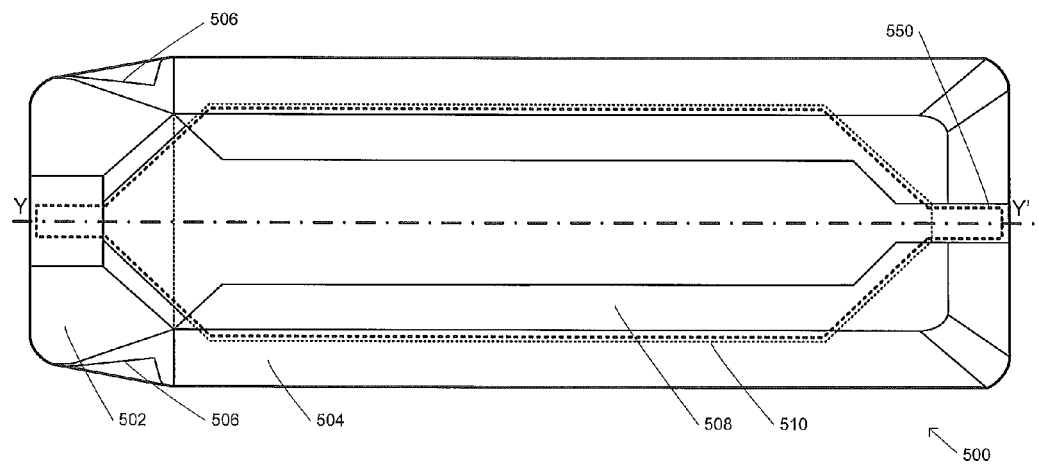
FIGS. 5A, 5B and 5C are illustrations of the heater unit of a specific embodiment of the fluid warming system of FIG. 2.
Figure 5B:
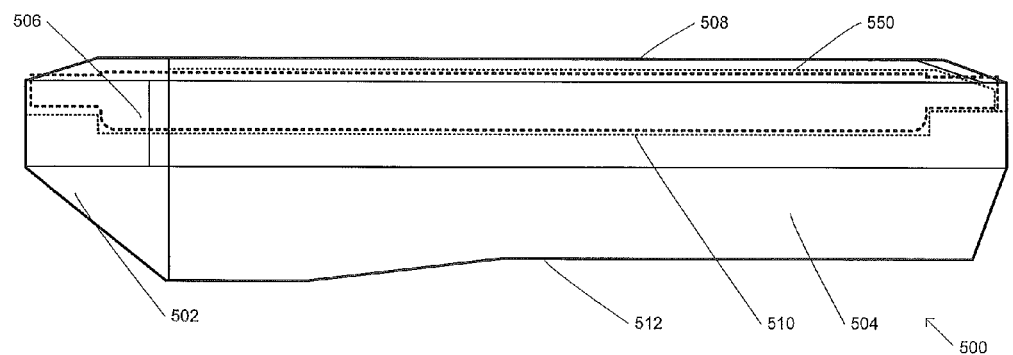
Figure 5C:
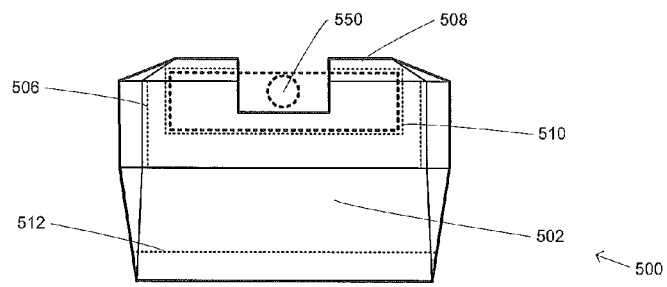
Figure 6A:
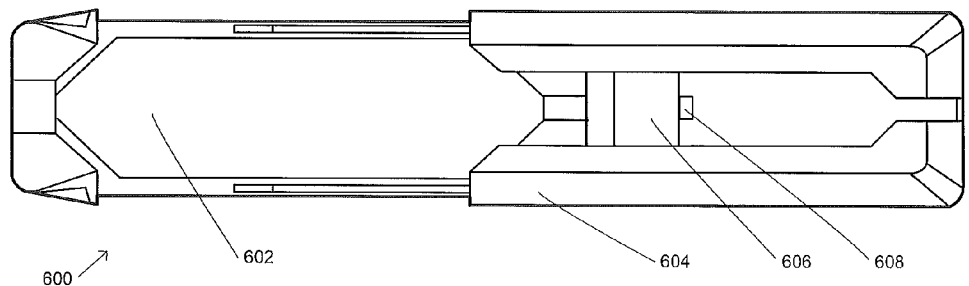
FIGS. 6A, 6B and 6C are illustrations of the insertion of the heat exchanger unit of FIGS. 4A-4C into the heater unit of FIGS. 5A-5C.
Figure 6B:
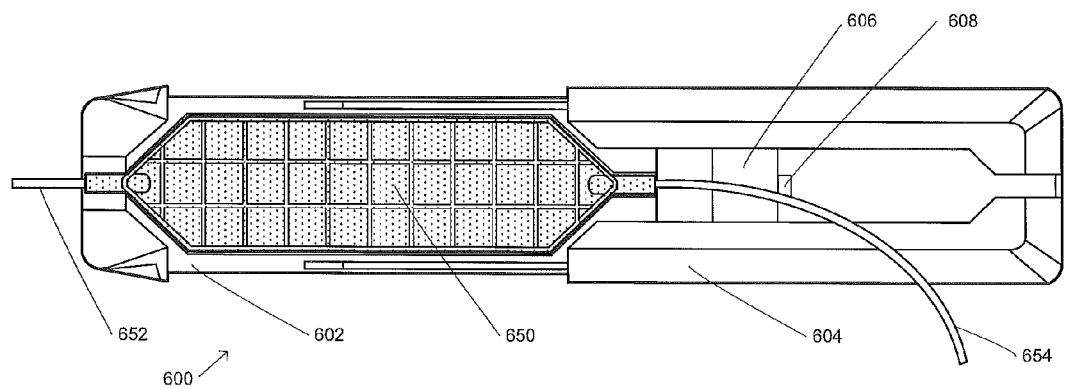
Figure 6C:
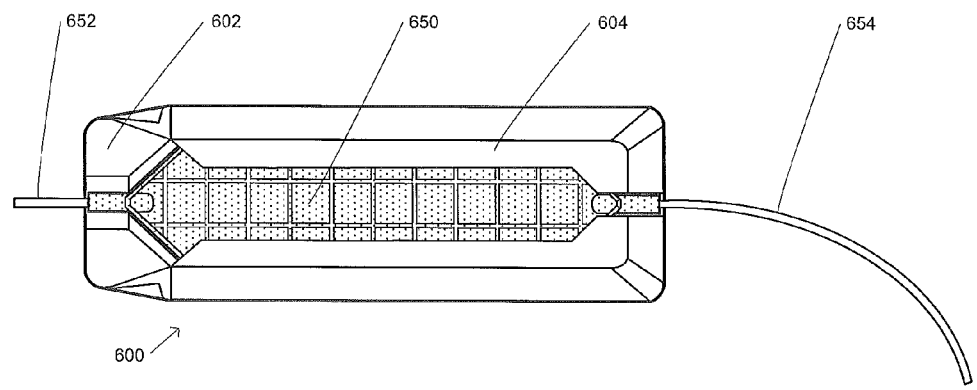

FIGS. 6A, 6B and 6C are illustrations showing the insertion of the heat exchanger unit of FIGS. 4A-4C into the heater unit of FIGS. 5A-5C.

In FIG. 6A, the heater unit 600 is shown empty and partially extended, prior to insertion of a cassette (heat exchanger unit). The fixed portion 602 and the sliding portion 604 of the heater unit 600 are indicated. Also visible on the lower interior surface of the sliding portion 602 are the wedge 606, whose shape follows the bottom surface of the sliding portion, and a small depression 608 providing a run-up section for the plunger (not shown), as described below.

In FIG. 6B, a cassette 650 is shown loaded into the heater unit 600. The cassette/transport unit 650 is shown with IV lines 652, 654 attached to the inlet and outlet respectively.

In FIG. 6C, the heater unit 600 is closed, causing the cassette 650 to be retained, sandwiched between the bottom surface of the top of the sliding portion 602 and a top surface in the recessed area of the fixed portion of the heater unit 600. Again the IV lines 652, 654 are shown. A catch (not shown) is provided to lock the device in the closed position, but other appropriate mechanisms or arrangements are of course possible.

Figure 7:
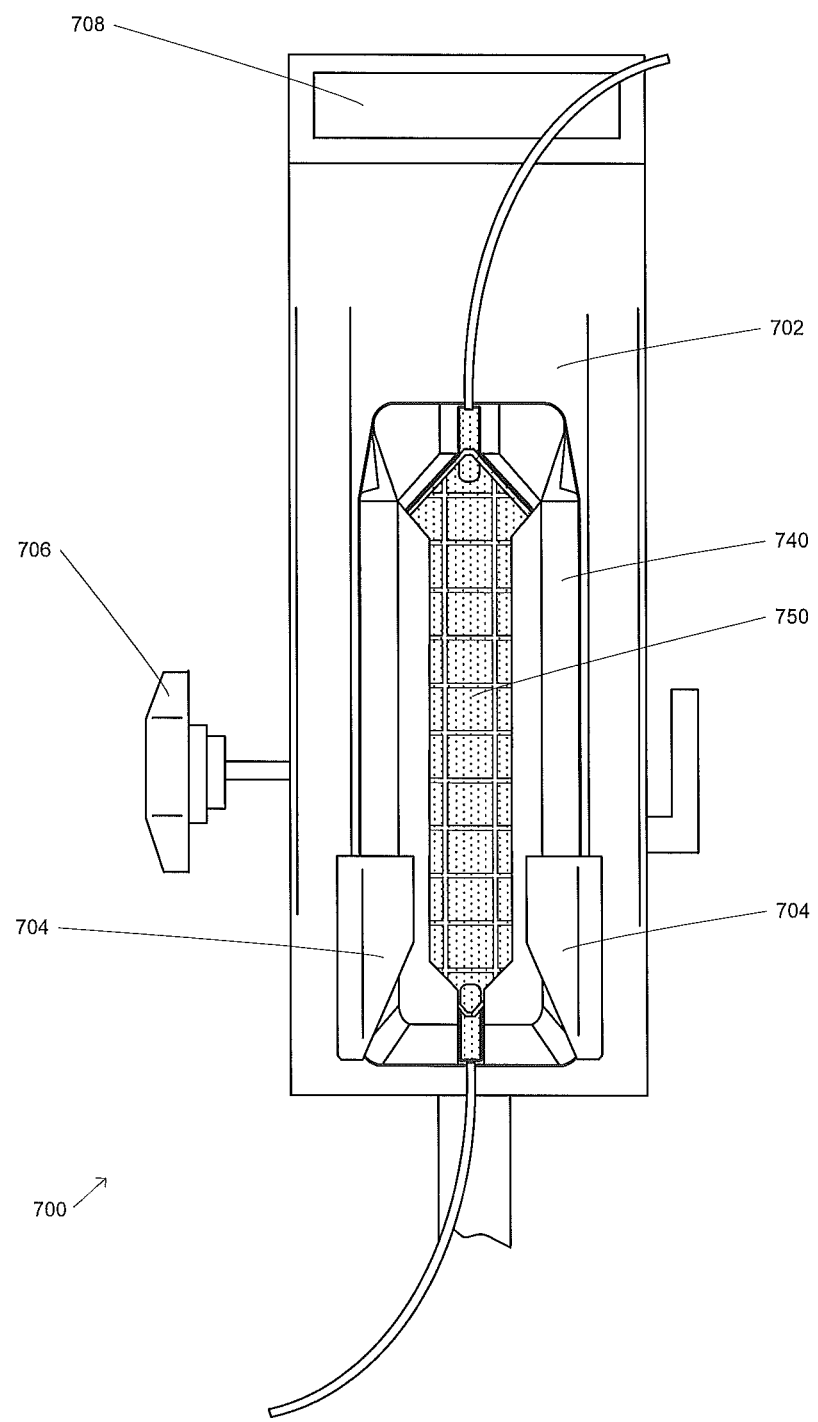
FIG. 7 is an illustration of the insertion of the heater unit and heat exchanger unit of FIG. 6C inserted into a docking cradle.

FIG. 7 is an illustration of the insertion of the heater unit and heat exchanger unit of FIG. 6C inserted into a docking cradle 700. The cradle includes a recessed portion 702 for receiving the heater unit 740, in turn including a disposable cassette 750. The cradle 700 also includes arms 704 for restraining the heater unit 740. Adjustment wheel 706 can be turned to clamp the unit 740 in place once it is set up. A set of controls 708 facilitates operation of the heater unit 740 and may incorporate additional controls for controlling the IV operation more generally. Power is supplied to the heater unit 740 via a connector in the cradle (not shown), although in a variant of the present embodiment the heater unit 740 is able to operate on battery power or via mains power provided otherwise.

Figure 8A:
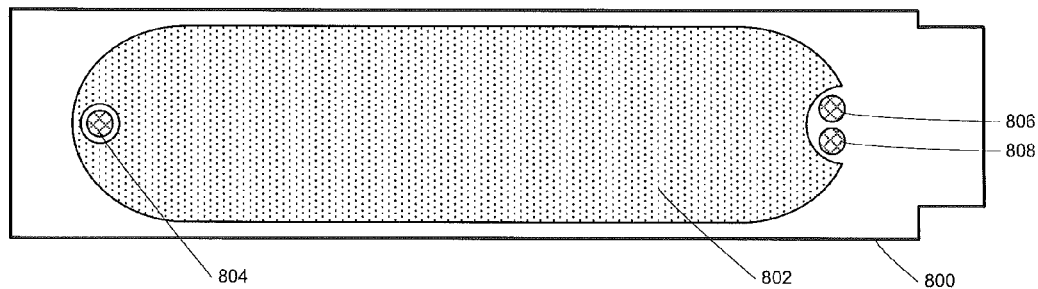
FIGS. 8A and 8B are schematic illustrations of a circuit board inside the heater unit of FIGS. 5A-5C.
Figure 8B:
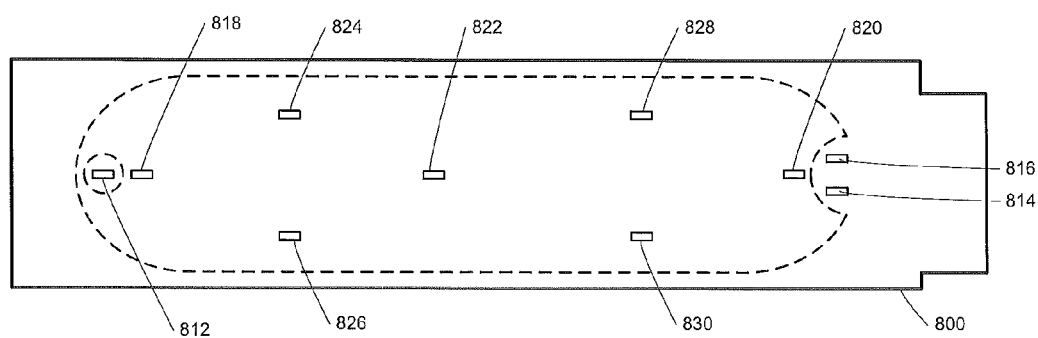

FIGS. 8A and 8B are schematic illustrations of a circuit board inside the heater unit of FIGS. 5A-5C. The circuit board in this embodiment includes essentially all heating and control functions (not shown), although additional components may typically be required for interfacing batteries or switching/rectifying/transforming mains power, and the like.

The board 800 in the present embodiment includes a thin film resistor type heater element 802, with gaps 804, 806, 808 in the heater element corresponding to the location of respective temperature sensors 812, 814, 816 on the reverse of the circuit board 800. Sensors 812, 814, 816 measure contact temperatures on the disposable cassette. Additional temperature sensors 818, 820, 822, 824, 826, 828, 830 are provided on the reverse of the heater element 802 for measuring the temperature of the heater element at different points, including in particular sensors 818 and 820 for measuring the heater temperature at the inlet and outlet respectively.

Figure 9:
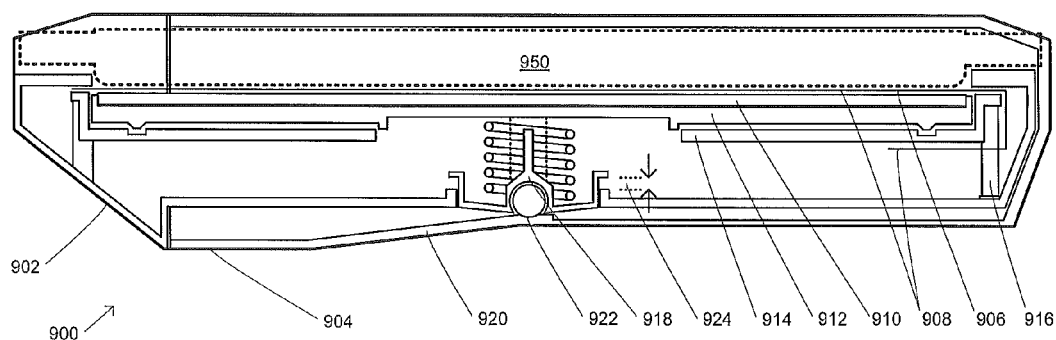
FIG. 9 is a schematic showing the cross-section Y-Y' of the heater unit of FIG. 5A.

FIG. 9 is a schematic showing the cross-section Y-Y' of the heater unit of FIG. 5A. Some dimensions are exaggerated for ease of understanding. As before, the heater unit 900 includes a fixed portion 902 and sliding portion 904, and the heat exchanger unit/disposable cassette 950 is shown in outline. In the present embodiment, the thermally conductive, insulating membrane 906 and the flex heater layer 908 are sandwiched together with thermal conductive paste, as mentioned earlier, and are represented in FIG. 9 by a single line due to their relative thinness. It will be noted that the heater layer 908 extends beyond the membrane 906 to the side and round underneath the assembly, at the right hand side of the figure, so as to provide appropriate electrical connections. As will be explained in more detail later, the membrane layer 906 (and heater layer 908) is clamped to the fixed portion 902 of the heater unit 900.

Underneath the clamped heater layer 908 and membrane layer 906 is provided the compressible foam layer 910, which is mounted on a stiff compression frame 912 (preferably formed from aluminium). The frame 912 rests on, and is guided within, a mid-frame 914, providing a backstop for the compression of the layers 906, 908, 910, 912 into the device. The mid-frame 914 is fastened to the top housing with screws, which compresses seals between the circumference of the flexible layers 906, 908 and the top housing (not shown). The screw pillars (including pillar 916) provide a guide for the assembly of the layers 906 and 908, as is explained later, as well as structural strength. A plunger 918 extends out of the base of the fixed portion 902 of the heater unit 900 and is shown in the engaged position, resting on the run-in 922, a depression at the top of the wedge 920 that is formed by the exterior shape of the sliding portion 904 of the heater unit 900. The plunger is at a maximum displacement, indicated at 924. A further flexible membrane (not shown) provides a seal between the heater unit body and the plunger (see below).

Figure 10:
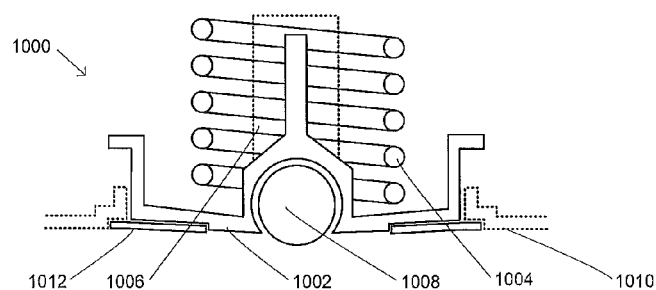
FIG. 10 is an enlarged view of the plunger and springs of FIG. 9.

FIG. 10 is an enlarged view of the plunger unit of FIG. 9. The plunger 1000 includes a plunger body 1002 in circular cross-section (not shown), and includes a heavy-duty spring 1004 providing approximately 100 N of force, for pressing the foam and heater assembly against the membrane and cassette when the cassette is loaded, and a secondary spring providing approximately 5 N of force for maintaining tension on the membrane layer when the heater unit is unloaded. In use, the plunger has a range of travel of approximately 3.5 mm. A wheel 1008 is provided to reduce friction forces acting between the plunger 1000 and the wedge (not shown). The cooperating portions 1010 of the base are shown, with a flexible membrane 1012 providing an appropriate seal. The figure is schematic and not to scale; it will be appreciated that the material, thickness, fastening method and width of the plunger membrane, and so on, can be selected to provide an appropriate strength and elasticity, and the shape of the cooperating portions of the plunger and heater body can be shaped as appropriate to provide a better seal and performance. The sealing membrane 1012 is formed from TPE plastic and injection-moulded onto the housing and plunger ("2K-moulding). The TPE material has good adherence/bonding with the ABS-PC of the plunger and housing. Silicon rubber is an appropriate alternative for the TPE material. In a variant, the membrane is shape-fitted and mechanically fixed to the membrane and housing. Alternatively, it may be glued to the housing and membrane. The main function of the membrane is to prevent water ingress via the gap between the plunger and the housing. It does not participate significantly in the pressure on the heat transfer membrane.

Alternative configurations and attachments of the membrane are of course possible. In an alternative embodiment, the plunger is at least partially replaced with an inflatable device, providing similar elastomeric properties. Other variants are of course possible.

Figure 11:
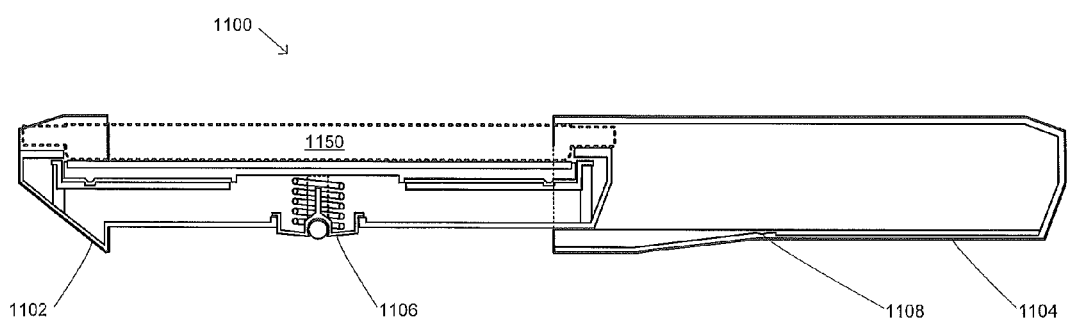
FIG. 11 is a schematic showing the cross-section Y-Y' of FIG. 9 with the heater unit case opened.

FIG. 11 is a schematic showing the cross-section Y-Y' of FIG. 9 with the heater unit case in opened configuration. The fixed portion 1102 and sliding portion 1104 of the heater unit 1100 are again shown, and the position of the cassette 1150 is shown in outline. Here it can be seen that the plunger 1106 is at its other extreme of displacement, and the primary spring no longer exerts force on the heater and foam assembly. The secondary spring still provides a small amount of compression, however, to maintain tension on the heat transfer membrane 906 of FIG. 9. Because of the shape of the base 1108 of the sliding portion 1104, the plunger 1106 does not contact the surface on which the unit 1100 rests.

Figure 12:
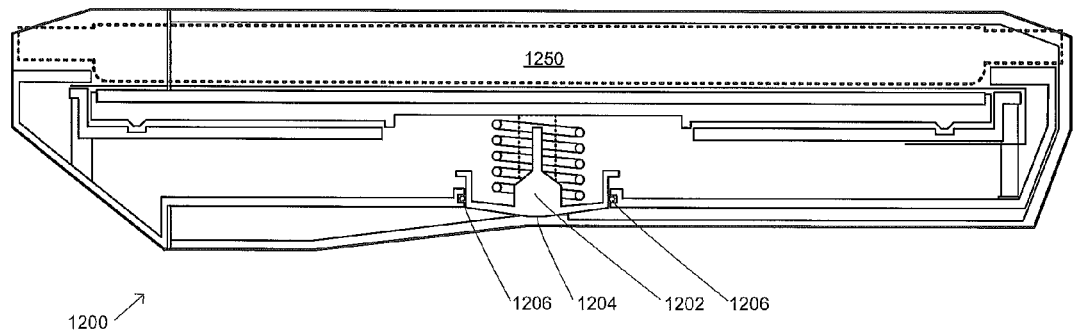
FIG. 12 is a schematic showing the cross-section Y-Y' of an alternative embodiment of the heater unit of FIG. 5A.

FIG. 12 is a schematic showing the cross-section Y-Y' of an alternative embodiment of the heater unit of FIG. 5A. As before, the heater unit 1200 and outline of the cassette 1250 are shown. The plunger 1202 in this embodiment does not have the wheel as before, but instead slides simply into the run-in area 1204. The decreased ease of use is offset by simpler maintenance and cleaning of the device. In addition, in this embodiment the flexible membrane providing a seal between plunger and heater unit body is replaced by an O-ring 1206, which the plunger is able to slide past in use. Other methods of sealing and cooperating between the plunger and body are of course possible; an X-ring may be used, for example. The different sealing method may be provided independently of the different plunger configuration.

Figure 13:
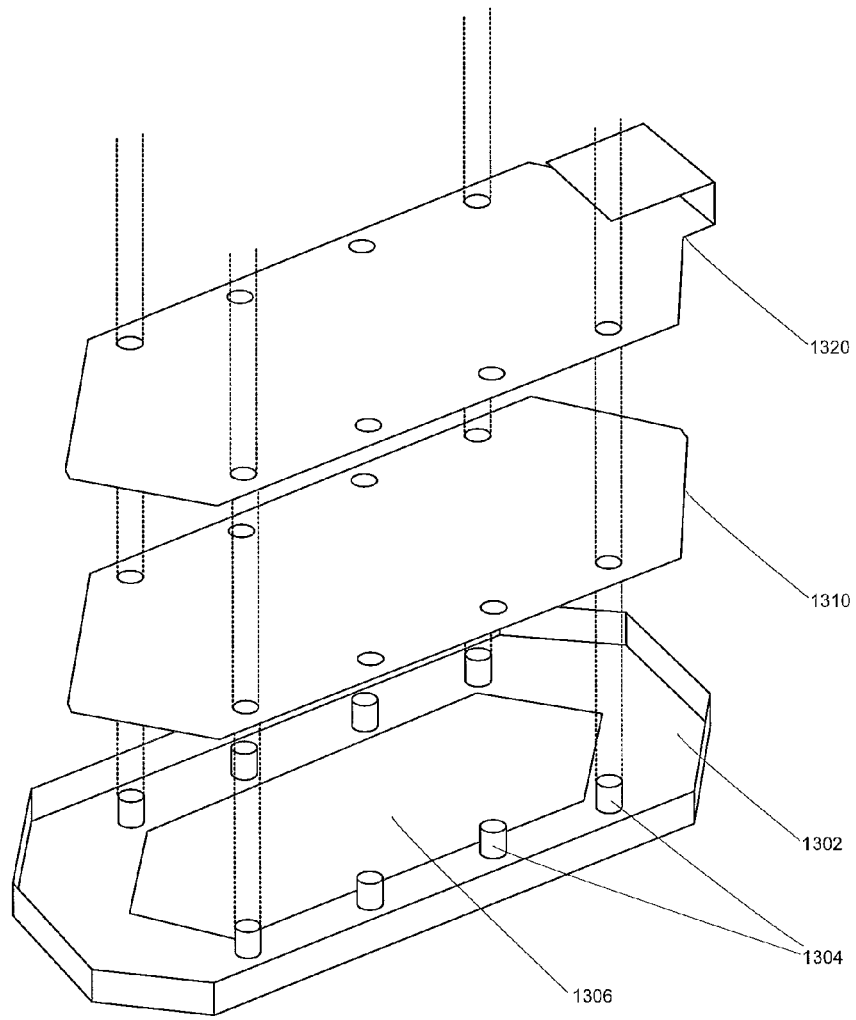
FIG. 13 is a schematic showing the assembly of part of the heater unit of FIGS. 5A-5C.

FIG. 13 is a schematic showing the assembly of part of the heater unit of FIGS. 5A-5C. A simplified version of the upper frame 1302 is shown (upside-down), with the screw pillars 1304 (for attachment of the mid-frame) serving as assembly guides for attaching the membrane layer 1310 and heater element layer 1320, corresponding to layers 906 and 908 respectively of FIG. 9. During assembly, adhesive is applied around the edge of aperture 1306, the layers are guided into position, and then secured further with seals that are compressed by screwing the mid-frame into the screw pillars, sandwiching the periphery of the layers 1320, 1310 between portions of the mid-frame and the upper frame 1302. Other methods of assembly are of course possible, for example omitting the adhesive.

Figure 14:
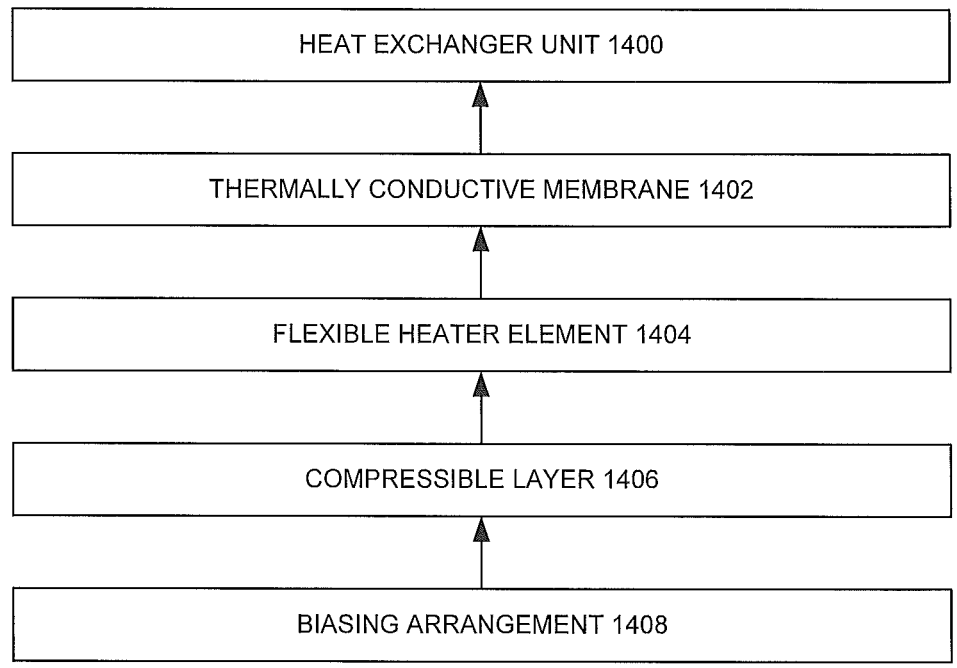
FIG. 14 is a schematic showing the formation of the membrane and eater layers of the heater unit of FIG. 9.

FIG. 14 is a schematic showing the formation of the heat transfer membrane 906 and heater layers of the heater unit of FIG. 9. The assembly and force path is shown in simpler terms, with the heat exchanger unit 1400 cooperating with the thermally conductive membrane 1402, which overlies the flexible heater element 1404, which in turn is supported by the compressible layer 1406, which is acted on by the biasing arrangement 1408, which in the present embodiment comprises the plunger and spring arrangement. In an alternative embodiment, where access to the inner part of the heater unit is restricted and/or the heat exchanger unit incorporates appropriate shielding, for example, the membrane 1402 is not required.

Figure 15:
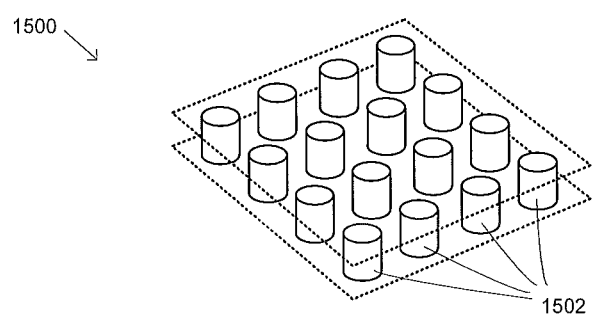
FIG. 15 is a schematic showing a portion of a compressible layer in a variant of the heater unit of FIGS. 5A-5C.

FIG. 15 is a schematic showing a portion of a compressible layer in a variant of the heater unit of FIGS. 5A-5C. In place of the silicon foam or other compressible foam, the compressible layer 1500 can be formed instead by a series of springs 1502. This can reduce the tendency for compression set.

Figure 16:
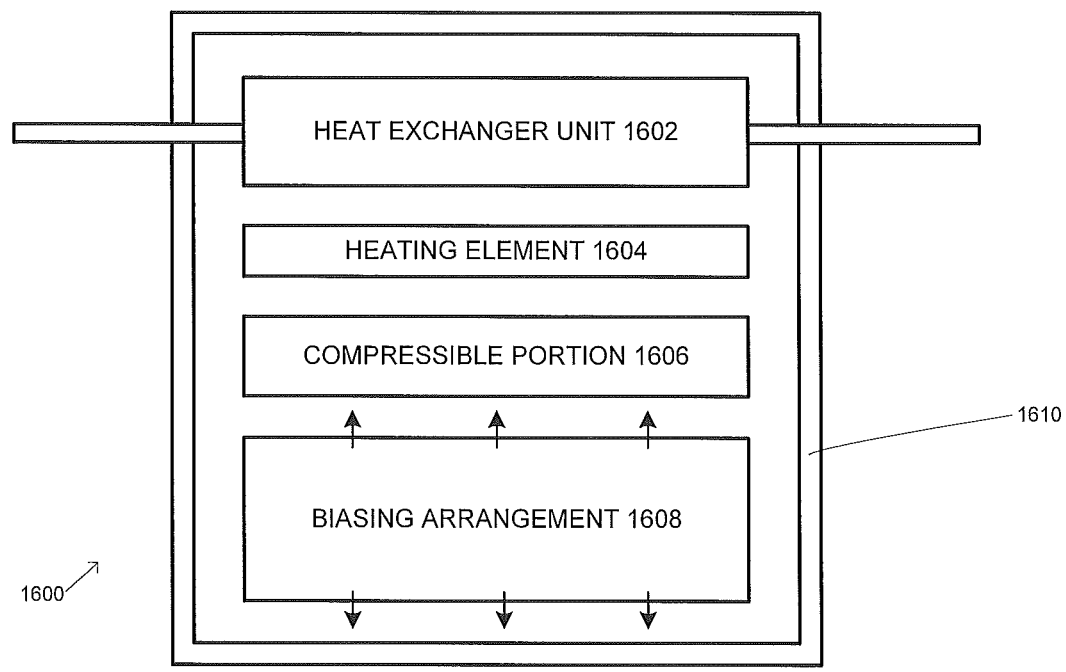
FIG. 16 is a further schematic showing the arrangement of elements within the fluid warming system of FIG. 1.

FIG. 16 is a further schematic showing the arrangement of elements within the fluid warming system of FIG. 1, showing the interrelationship between the elements in simplified form.

The fluid warming system 1600 as before includes a heat exchanger unit 1602 adjacent to a heating element 1604, which is in turn adjacent to a compressible portion 1606 (for example a foam or gel layer), which is in turn adjacent to a biasing arrangement 1608 (which may for example be the springs or the various other biasing means mentioned above), which reacts (at least indirectly) against the inner top and bottom surfaces of the body 1610 of the heater unit, so as to apply a transverse compression force across the compressible portion 1606, heating element 1604 and heat exchanger unit 1602, as discussed above. A rigid support layer (not shown) usually forms part of the biasing arrangement so as to assist in the uniform transmission of the compression force across the compressible portion 1606 and so on. Additional elements of the biasing arrangement 1608 may be provided in other locations than that shown, such as a planar surface or rigid support layer on the distal side of the heat exchanger unit 1602 relative to the heating element 1604, and so on.

Figure 17:
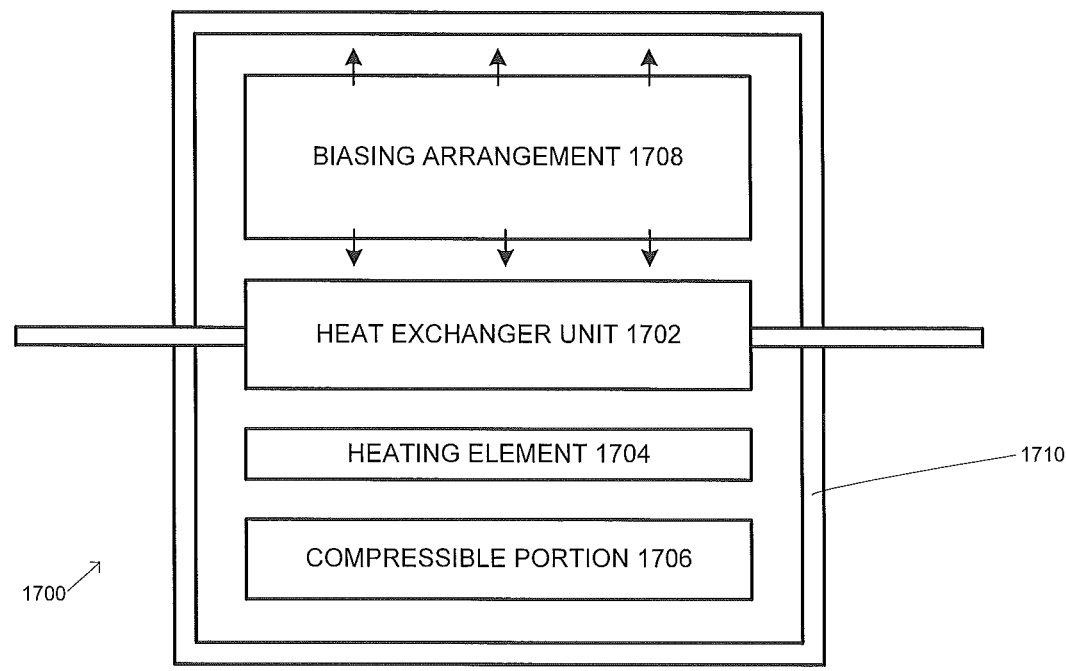
FIG. 17 is a schematic showing an arrangement of elements within a further embodiment of a fluid warming system.

FIG. 17 is a schematic showing an arrangement of elements within a further embodiment of a fluid warming system, showing the interrelationship between the elements in simplified form.

The heater unit 1700 of the fluid warming system includes a heat exchanger unit 1702, heating element 1704, compressible portion 1706 and biasing arrangement 1708, reacting (at least indirectly) against the inner top and bottom surfaces of the body 1710 of the heater unit. In this arrangement, the (bulk of the) biasing arrangement is provided above the heat exchange unit rather than below the compressible portion 1706. The main portion of the biasing arrangement 1708 may for example be mounted in the slideable cover and activated when the cover is closed to retain the heat exchanger unit 1702. As before, additional elements of the biasing arrangement 1708 may be provided elsewhere, such as a planar surface or 'floating' compression frame below the compressible portion 1706.

Figure 18:
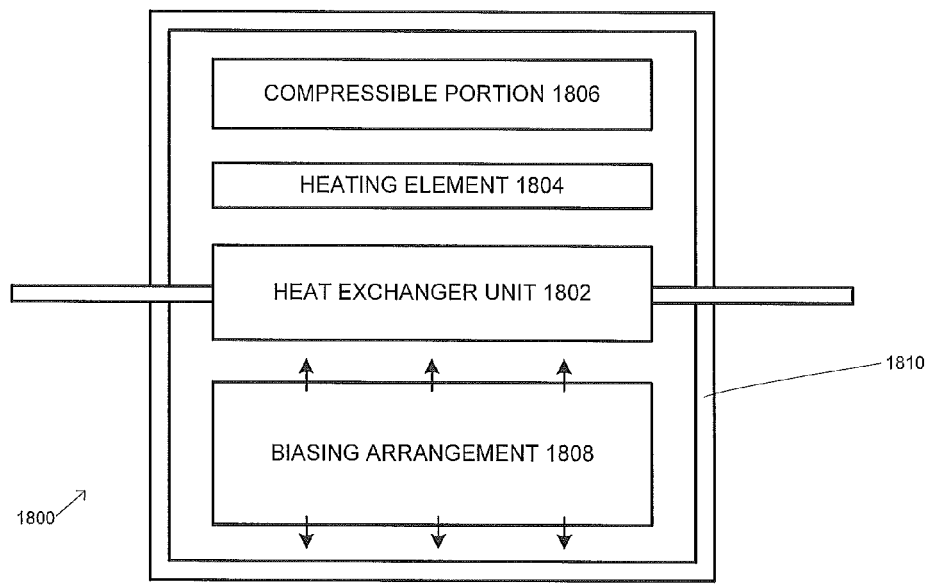
FIG. 18 is a schematic showing an arrangement of elements within a yet further embodiment of a fluid warming system.

FIG. 18 is a schematic showing an arrangement of elements within a yet further embodiment of a fluid warming system, showing the interrelationship between the elements in simplified form.

The heater unit 1800 of the fluid warming system as before includes a heat exchanger unit 1802, heating element 1804, compressible portion 1806 and biasing arrangement 1808, reacting (at least indirectly) against the inner top and bottom surfaces of the body 1810 of the heater unit. In this arrangement, the (bulk of the) biasing arrangement is provided below the heat exchange unit, as in the main embodiment, and the heating element and compressible portion 1806 are in this case provided above the heat exchanger unit 1802. The heating element 1804 and compressible portion 1806 may for example be mounted in the slideable cover and activated when the cover is closed to retain the heat exchanger unit 1802. As before, additional elements of the biasing arrangement 1808 may be provided elsewhere, such as a planar surface or 'floating' compression frame above the compressible portion 1806 (mounted in or forming part of the body 1810, for example).

Other arrangements of the elements mentioned above (and additional elements) are of course possible.

Figure 19:
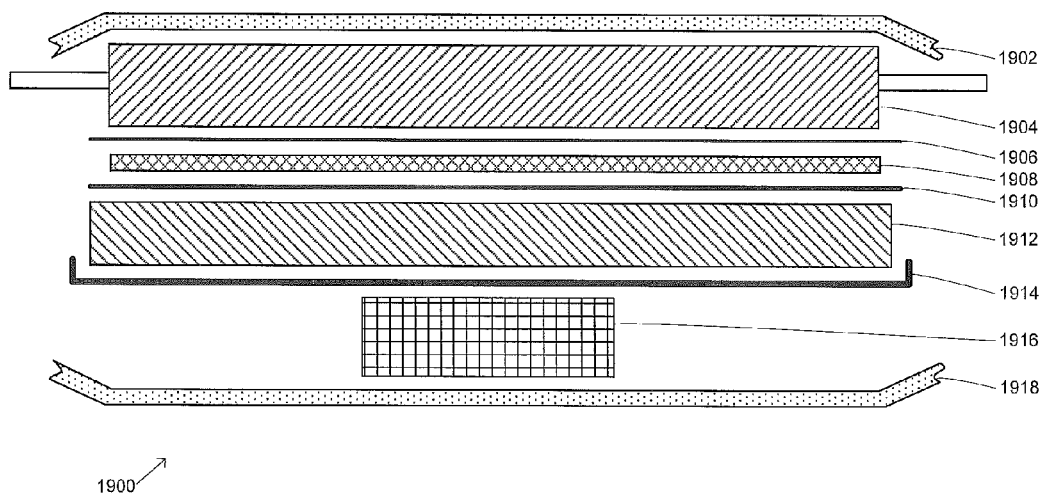
FIG. 19 is an alternative view of the elements within the fluid warming system of FIG. 1.

FIG. 19 is an alternative view of the elements within the fluid warming system of FIG. 1, again showing the interrelationship between the elements in simplified form. The arrangement in FIG. 19 corresponds to a simplified view of the heater unit 1900 of the fluid warming system shown in FIG. 9, showing the various layers of the device in overview. Layers are shown with exaggerated scale and artificially separated for clarity.

In descending sequence within the figure can be seen the layers of: the top portion 1902 of the heater unit body/housing, the heat exchanger unit 1904, a thin and reasonably flexible electrically insulating layer 1906 (with relatively good thermal conduction properties), a heat conductive paste layer 1908, a flexible heater 1910, a compressible foam/gel layer (possibly a fluid bag) 1912, a rigid support layer (compression frame) 1914, a spring arrangement (or other biasing system) 1916, and the bottom portion 1918 of the heater unit body/housing. In use, the elements are sandwiched together so that the spring/biasing arrangement 1916 causes a uniform compression force to be applied across the other layers shown, within the body/housing 1902, 1918.

Figure 20:
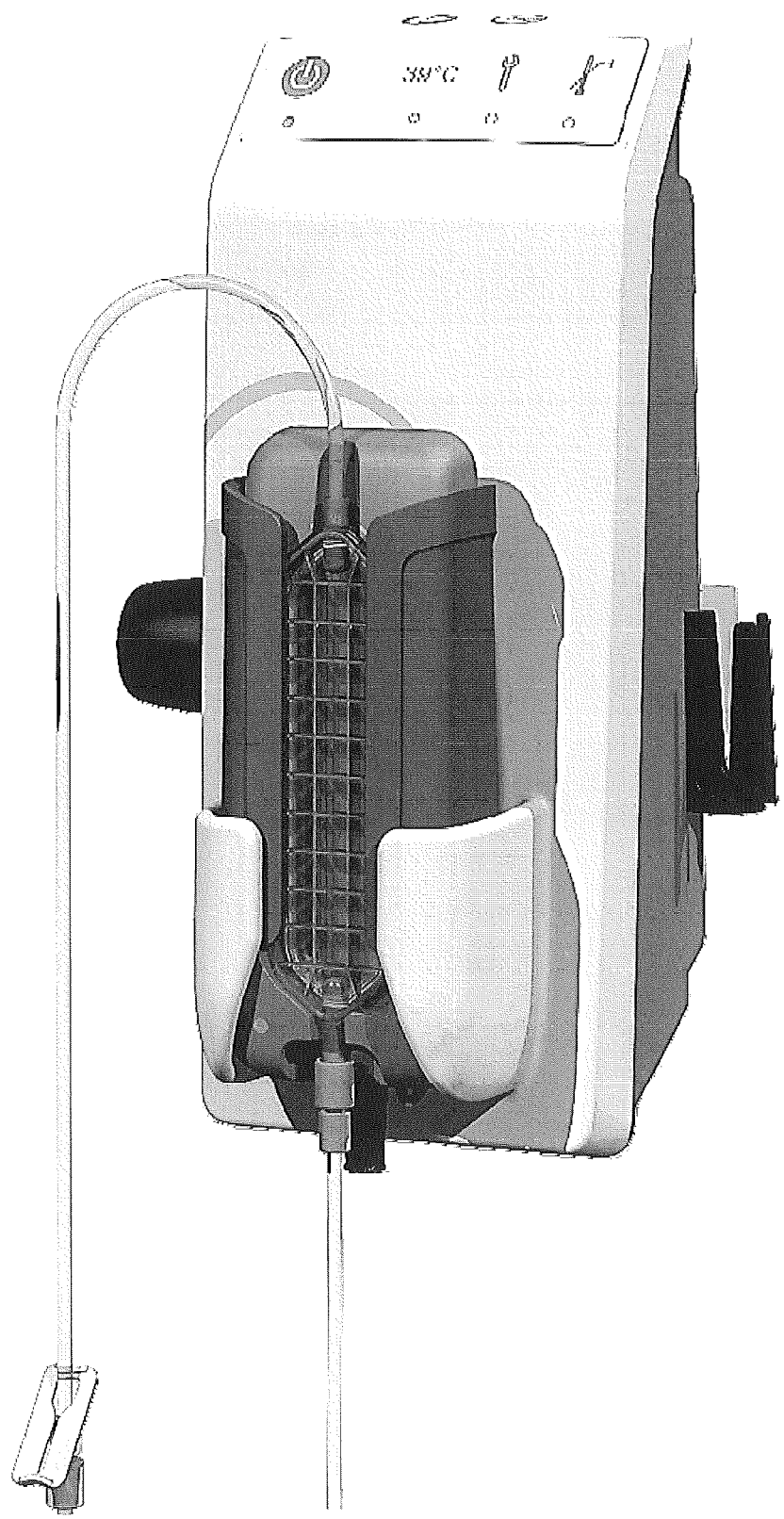
FIG. 20 is a perspective drawing of another embodiment of a fluid warming system, including a heater unit, heat exchanger unit and docking cradle.

FIG. 20 is a perspective drawing of another embodiment of a fluid warming system, including a heater unit, heat exchanger unit and docking cradle. The heat exchanger unit is shown mounted within the heater unit, and the heater unit is shown mounted within the docking cradle, in turn. In addition, two IV lines are shown (partially) to demonstrate the use of the device. The arrangement is essentially the same as that depicted in FIG. 7 in relation to the first embodiment.

The embodiment of FIGS. 20 to 25 differs from the first embodiment shown in FIGS. 1 to 14, and in mostly cosmetic and ergonomic ways, for example in relation to the shape of the case. The shape of the present embodiment was preferred as giving a better trade-off between performance and usability, and complexity and cost (for example).

Figure 21:
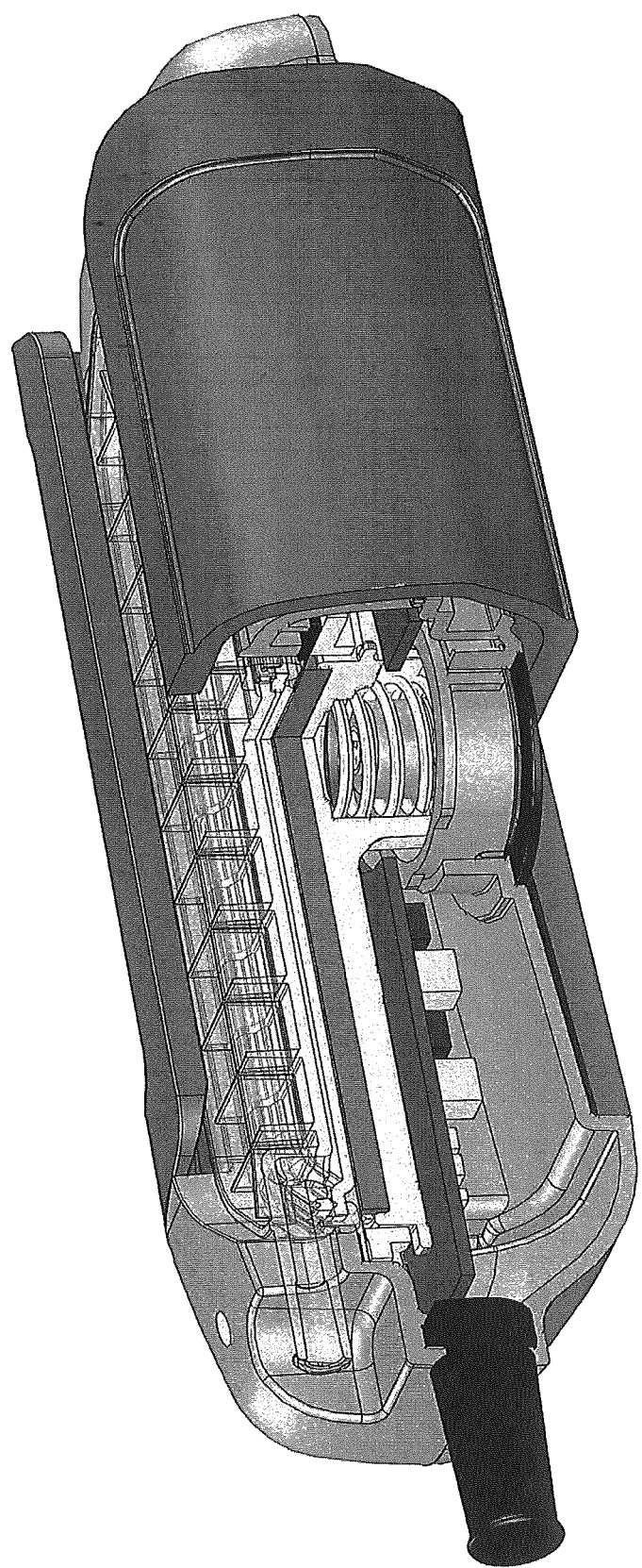
FIG. 21 is a perspective section through the heater unit and heat exchanger unit of FIG. 20.

FIG. 21 is a perspective section through the heater unit and heat exchanger unit of FIG. 20, showing the location of the plunger relative to other parts of the device.

Figure 22:
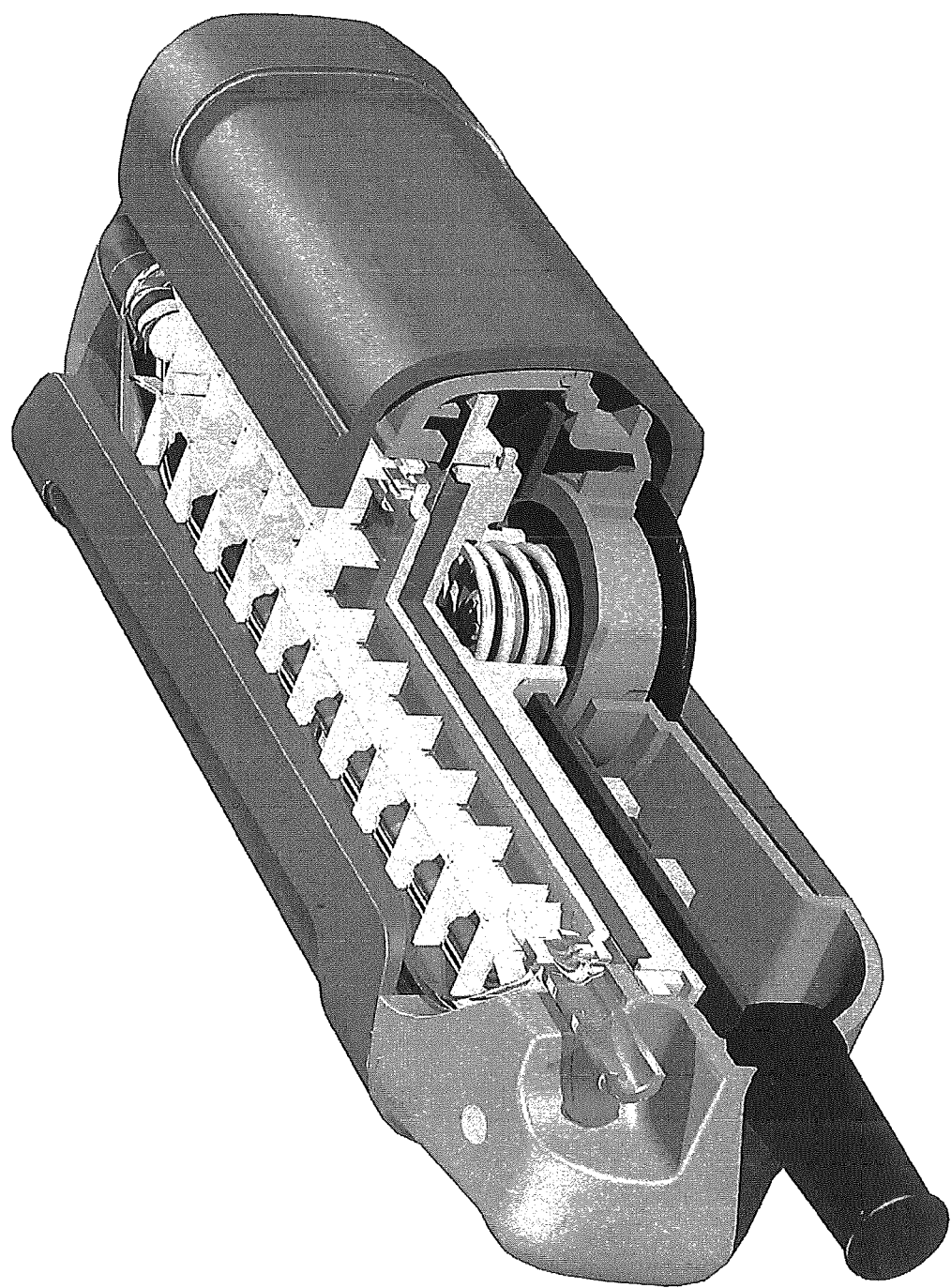
FIG. 22 is a further perspective section through the heater unit and heat exchanger unit of FIG. 20.

FIG. 22 is a further perspective section through the heater unit and heat exchanger unit of FIG. 20.

Figure 23:
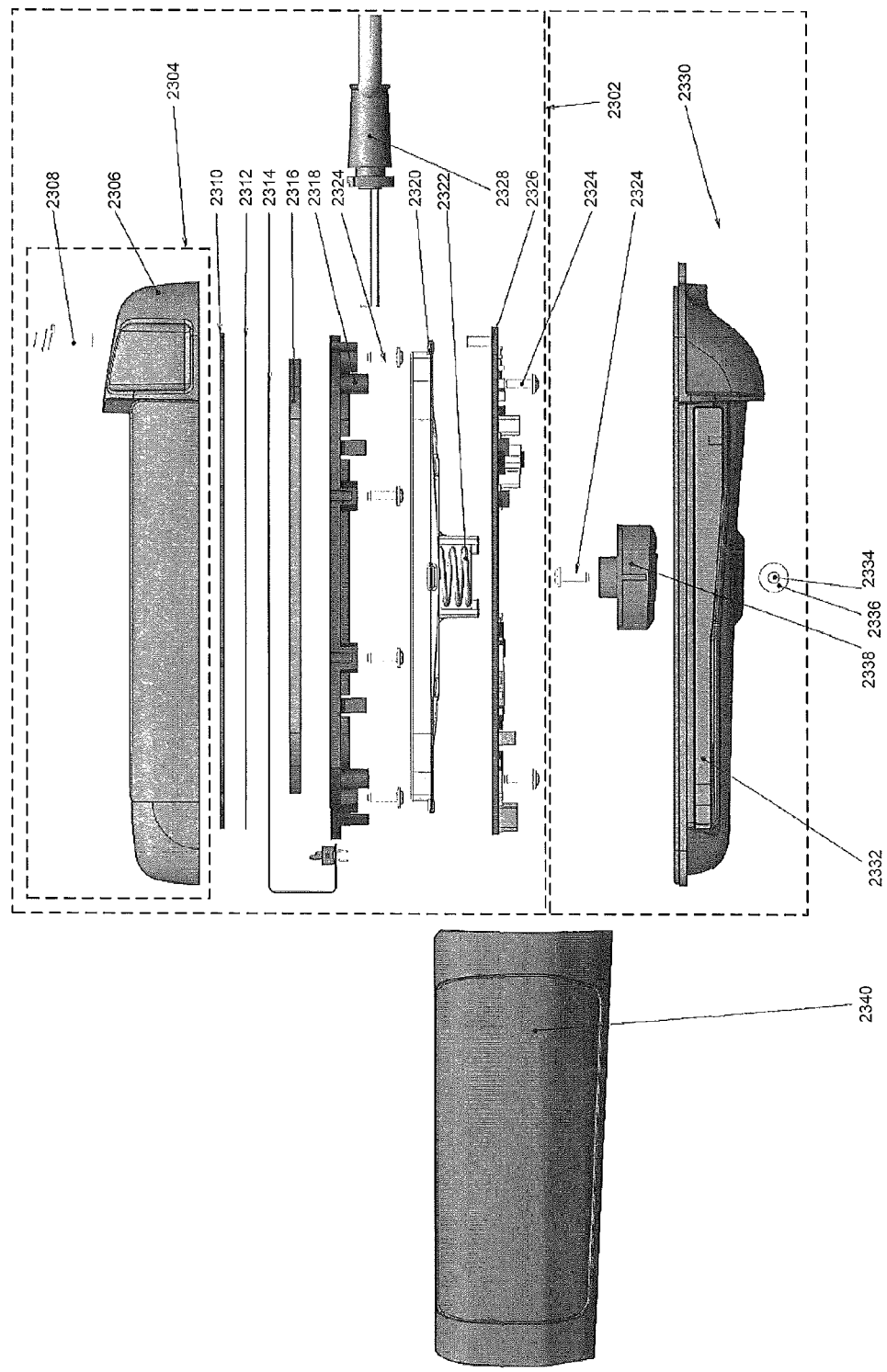
FIG. 23 is an exploded schematic of the heater unit of FIG. 20.

FIG. 23 is an exploded schematic of the heater unit of FIG. 20. The present figure corresponds approximately to a disassembled version of the first embodiment shown in FIG. 9.

In more detail, in FIG. 23 is shown a top assembly 2302, a top cover and lightguide assembly 2304, the upper cover 2306, the light guide 2308, a foil seal 2310, an 0.075 mm thickness sheet of Kapton® (or similar polyimide) 2312, a heater assembly 2314, a foam layer 2316, an inner frame 2318, a chassis 2320, a spring activator 2322, Ejot® screws WN5451 25X8 (or similar screw or other fastener) 2324, a PCB assembly 2326, a cable assembly 2328, a bottom assembly 2330, an overmoulded lower cover 2332, a plunger shaft 2334, a guiding wheel 2336, an activator 2338, and a slider 2340.

Figure 24:
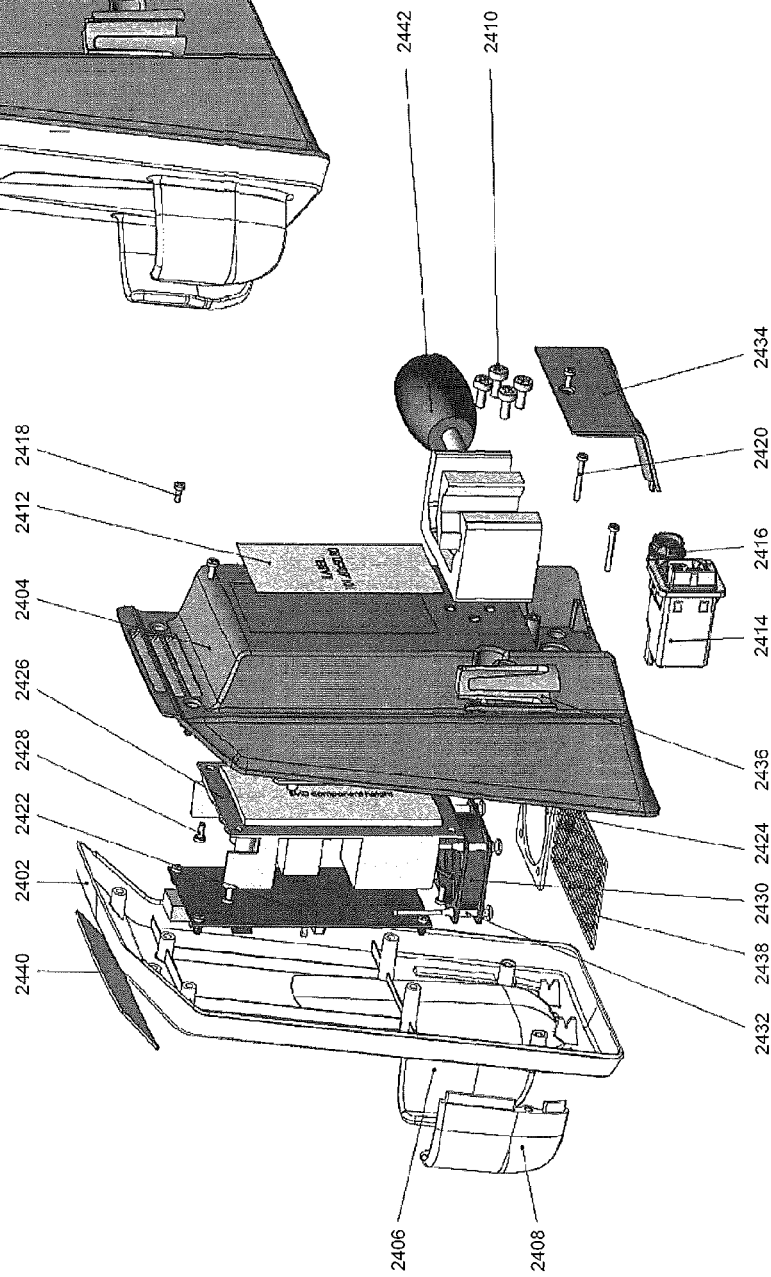
FIG. 24 is an exploded schematic of the docking cradle of FIG. 20.

FIG. 24 is an exploded schematic of the docking cradle of FIG. 20.

In more detail, in FIG. 24 is shown a front cover 2402, a back cover 2404, a left cradle 2306, a right cradle 2308, a screw of type M5x12 (or similar screw or other fastener) 2310, a label 2312, a network connector 2314, a data port 2316, a screw of type M3x8 (or similar fastener, and so on) 2318, a screw of type M3x25 (or similar fastener) 2320, board 2322, a frame plate 2324, a power supply 2326, a screw of type M3x8 (or similar fastener) 2328, a fan 2330, a damper 2332, a connector plate 2334, a drip chamber holder 2336, a baffle plate 2338, a front label 2340 and a clamp 2342.

Figure 25:
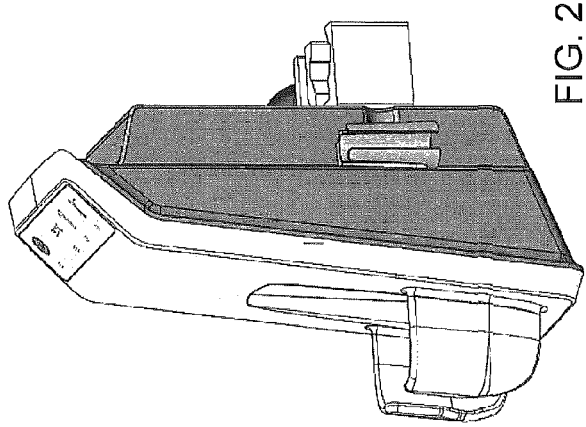
FIG. 25 is a schematic of the docking cradle of FIG. 20 as assembled.

FIG. 25 is a schematic of the docking cradle of FIG. 20 when assembled.

Although the embodiments above predominantly relate to warming IV fluids, it will be appreciated that the same principles can be applied for example to warming bodily or other fluids for other purposes (for example to treat hypothermia), or used in-situ in industrial processes, and so on. The embodiment can be adapted, for example, to any appropriate application in which a separate part needs to be heated by conductive heating. Additionally, it will be appreciated that the described embodiments can be adapted for applications which do not have a replaceable or separate part, but instead have an integral fluid conduit.

Although the present invention has been described above with reference to specific embodiments, it will be apparent to a skilled person in the art that modifications lie within the spirit and scope of the present invention.

The invention claimed is:
1. An intravenous fluid warmer comprising:
a body portion for receiving a heat exchanger unit, said heat exchanger unit being operable to receive the intravenous fluid;
a flexible heating element which, in use, makes thermal contact with a heat transfer surface of the heat exchanger unit;
a compressible portion disposed on the distal side of the flexible heating element relative to the heat exchanger unit when received;
a biasing arrangement operable, in use, to distribute a transverse compression force across the arrangement formed from the compressible portion, the heating element and the heat exchanger unit, whereby the compression force causes the heating element to be urged towards the heat transfer surface of the heat exchanger unit and the compressible portion, in conjunction with the compression force, causes the heating element to conform more closely to the shape of the heat transfer surface; and
a retaining arrangement for releasably retaining the heat exchanger unit, said retaining arrangement including a moveable arrangement including at least one of a sliding portion, lever, and rack and pinion arrangement, and wherein said moveable arrangement is operable to transmit a force to the biasing arrangement by means of a wedge and plunger.

2. A heater unit comprising:
a body portion for receiving a heat exchanger unit, said heat exchanger unit being operable to receive a fluid to be heated;
a flexible heating element which, in use, makes thermal contact with a heat transfer surface of the heat exchanger unit;
a compressible portion disposed on the distal side of the flexible heating element relative to the heat exchanger unit when received;
a biasing arrangement operable, in use, to distribute a transverse compression force across the arrangement formed from the compressible portion, the heating element and the heat exchanger unit, whereby the compression force causes the heating element to be urged towards the heat transfer surface of the heat exchanger unit and the compressible portion, in conjunction with the compression force, causes the heating element to conform more closely to the shape of the heat transfer surface; and
a retaining arrangement for releasably retaining the heat exchanger unit, said retaining arrangement including a moveable arrangement including at least one of a sliding portion, lever, and rack and pinion arrangement, and wherein said moveable arrangement is operable to transmit a force to the biasing arrangement by means of a wedge and plunger.

3. A heater unit according to claim 2, further comprising a thermally-conductive membrane which, in use, physically contacts the heat exchanger unit and separates the heat exchanger unit from the heating element.

4. A heater unit according to claim 2, wherein the membrane is attached to the body portion.

5. A heater unit according to claim 2, wherein the retaining arrangement is operable to increase the compression force when the heat exchanger unit is retained by the retaining arrangement.

6. A heater unit according to claim 2, wherein the plunger includes a rotating member which, in use, is in contact with the wedge.

7. A heater unit according to claim 2, wherein the biasing arrangement is operable to maintain a minimum compression force when the heat exchanger unit is not retained by the retaining arrangement.

8. A heater unit according to claim 2, wherein the biasing arrangement comprises a first spring and preferably further comprises a second spring, the second spring providing a smaller compression force than the first spring across a wider range of operating conditions.

9. A heater unit according to claim 2, wherein the biasing arrangement reacts against the body portion.

10. A heater unit according to claim 2, wherein the biasing arrangement comprises an inflatable member.

11. A heater unit according to claim 2, wherein the compressible portion includes at least one of a flexible foam, a plurality of springs, flexible rubber and flexible plastic.

12. A heater unit according to claim 2, further comprising a rigid support layer for distributing the compression force across the compressible portion.

13. A heater unit according to claim 2, wherein, in use, the body portion encloses the heat exchanger unit.

14. A fluid warming system comprising a heater unit and at least one heat exchanger unit configured for use with said heater unit, wherein the heater unit comprises:
- a body portion for receiving a heat exchanger unit, said heat exchanger unit being operable to receive a fluid;
- a flexible heating element which, in use, makes thermal contact with a heat transfer surface of the heat exchanger unit;
- a compressible portion disposed on the distal side of the flexible heating element relative to the heat exchanger unit when received;
- a biasing arrangement operable, in use, to distribute a transverse compression force across the arrangement formed from the compressible portion, the heating element and the heat exchanger unit, whereby the compression force causes the heating element to be urged towards the heat transfer surface of the heat exchanger unit and the compressible portion, in conjunction with the compression force, causes the heating element to conform more closely to the shape of the heat transfer surface; and
- a retaining arrangement for releasably retaining the heat exchanger unit, said retaining arrangement including a moveable arrangement including at least one of a sliding portion, lever, and rack and pinion arrangement, and wherein said moveable arrangement is operable to transmit a force to the biasing arrangement by means of a wedge and plunger.

15. A system according to claim 14, wherein the heat exchanger unit is configured such that, in use, the fluid flows continuously through the heat exchanger.

16. A system according to claim 14, wherein the heat exchanger is configured such that, in use, the fluid is in direct contact with the heat exchanger unit.

17. A system according to claim 14 for warming intravenous fluids.

18. A system according to claim 14, wherein the plunger includes a rotating member which, in use, is in contact with the wedge.

19. An intravenous fluid warmer according to claim 1, wherein the plunger includes a rotating member which, in use, is in contact with the wedge.

* * * * *